(12) United States Patent
DePalma et al.

(10) Patent No.: US 11,391,717 B2
(45) Date of Patent: *Jul. 19, 2022

(54) CHARACTERIZATION AND CONTROL SYSTEM AND METHOD FOR A RESIN

(71) Applicant: General Electric Company, Schenectady, NY (US)

(72) Inventors: Stephanie Lynn DePalma, Miamisburg, OH (US); Michael Joseph O'Brien, Halfmoon, NY (US); Brittany Nicole Potter, West Chester, OH (US)

(73) Assignee: General Electric Company, Schenectady, NY (US)

( * ) Notice: Subject to any disclaimer, the term of this patent is extended or adjusted under 35 U.S.C. 154(b) by 177 days.

This patent is subject to a terminal disclaimer.

(21) Appl. No.: 16/512,787

(22) Filed: Jul. 16, 2019

(65) Prior Publication Data

US 2019/0339249 A1 Nov. 7, 2019

Related U.S. Application Data

(63) Continuation of application No. 15/291,253, filed on Oct. 12, 2016, now Pat. No. 10,408,812.

(51) Int. Cl.

| | | |
|---|---|---|
| *G01N 33/44* | (2006.01) | |
| *B29C 64/393* | (2017.01) | |
| *B33Y 50/02* | (2015.01) | |
| *G01N 21/27* | (2006.01) | |
| *G01N 21/359* | (2014.01) | |

(Continued)

(52) U.S. Cl.
CPC ......... *G01N 33/442* (2013.01); *B29C 64/393* (2017.08); *B33Y 30/00* (2014.12); *B33Y 50/02* (2014.12); *G01N 21/272* (2013.01); *G01N 21/359* (2013.01); *G01N 2021/3595* (2013.01)

(58) Field of Classification Search
None
See application file for complete search history.

(56) References Cited

U.S. PATENT DOCUMENTS

| | | | |
|---|---|---|---|
| 5,291,030 A | | 3/1994 | Brors |
| 5,417,853 A | * | 5/1995 | Mizuno .................. G01N 30/88 |
| | | | 210/143 |

(Continued)

FOREIGN PATENT DOCUMENTS

| | | |
|---|---|---|
| CN | 1876355 A | 12/2006 |
| CN | 105082533 A | 11/2015 |

(Continued)

OTHER PUBLICATIONS

Combined Chinese Office Action and Search Report Corresponding to Application No. 201780076349 dated Dec. 1, 2020.

(Continued)

*Primary Examiner* — Rufus L Phillips
(74) *Attorney, Agent, or Firm* — Dority & Manning, P.A.

(57) ABSTRACT

The present disclosure is directed to a method of altering chemical properties of an in-process resin used with a 3D printing apparatus. The method includes monitoring the in-process resin using an imaging spectrometer, comparing the in-process resin and a model using one or more spectrums from the imaging spectrometer, and diluting the in-process resin with a diluting resin.

18 Claims, 6 Drawing Sheets

(51) Int. Cl.
*G01N 21/35* (2014.01)
*B33Y 30/00* (2015.01)

(56) References Cited

U.S. PATENT DOCUMENTS

| | | | | |
|---|---|---|---|---|
| 5,729,333 | A * | 3/1998 | Osten | A61B 5/14535 |
| | | | | 356/39 |
| 5,849,595 | A * | 12/1998 | Alfano | G01N 21/6428 |
| | | | | 436/164 |
| 6,437,082 | B1 * | 8/2002 | McCracken | B01J 19/0006 |
| | | | | 528/196 |
| 9,176,061 | B2 * | 11/2015 | Maandi | C08J 3/248 |
| 2002/0010400 | A1 * | 1/2002 | Camacho | A61B 6/4085 |
| | | | | 600/473 |
| 2002/0128398 | A1 * | 9/2002 | Dessipri | G01N 21/3577 |
| | | | | 526/59 |
| 2003/0028355 | A1 * | 2/2003 | Minati | G01N 21/359 |
| | | | | 702/188 |
| 2007/0074659 | A1 * | 4/2007 | Wahlstrom | B29C 64/153 |
| | | | | 118/679 |
| 2010/0140852 | A1 | 6/2010 | Kritchman et al. | |
| 2012/0065755 | A1 | 3/2012 | Steingart et al. | |
| 2014/0152984 | A1 * | 6/2014 | Yoshida | C08L 63/00 |
| | | | | 356/306 |
| 2015/0321421 | A1 | 11/2015 | Ding | |
| 2016/0041090 | A1 * | 2/2016 | Kimura | B05D 3/067 |
| | | | | 427/553 |
| 2016/0193696 | A1 | 7/2016 | McFarland et al. | |
| 2016/0375676 | A1 * | 12/2016 | Ritchie | B29C 64/118 |
| | | | | 428/29 |
| 2018/0029311 | A1 * | 2/2018 | Depalma | B29C 64/307 |
| 2019/0322033 | A1 * | 10/2019 | Willis | B29C 64/124 |

FOREIGN PATENT DOCUMENTS

| | | | |
|---|---|---|---|
| CN | 105658356 A | 6/2016 | |
| JP | H07-260688 A | 10/1995 | |
| JP | H07260688 A | 10/1995 | |
| JP | 2012/173183 A | 9/2012 | |
| WO | WO-2011126044 A1 * | 10/2011 | B29C 59/046 |
| WO | WO2015/025171 A2 | 2/2015 | |

OTHER PUBLICATIONS

PCT ISR Corresponding to PCT/US2017/50578 dated Nov. 17, 2017.
Machine Translated Japanese Search Report Corresponding to Application No. 2019519975 dated Jun. 16, 2020.
Machine Translated Japanese Office Action Corresponding to Application No. 2019519975 dated Jul. 9, 2020.

* cited by examiner

| RESIN GRADE | INITIATOR PEAK RATIO RANGE | REACTIVE PEAK RATIO RANGE | SAMPLING FREQUENCY |
|---|---|---|---|
| 1 | $< I_1$ | $< R_1$ | |
| 2 | $I_1 - I_2$ | $R_1 \geq$ | |
| 3 | $I_2 - I_3$ | $R_2 \geq$ | |
| 4 | $I_3 - I_4$ | $R_3 \geq$ | |
| 5 | $I_4 - I_N$ | $R_4 \geq$ | |
| ⋮ | ⋮ | ⋮ | ⋮ |
| N | $I_{N-1} - I_N$ | $R_{N-1} \geq$ | |

CHARACTERIZATION AND CONTROL SYSTEM AND METHOD FOR A RESIN

CROSS REFERENCE TO RELATED APPLICATIONS

This Application claims priority to, and is a continuation application of, U.S. patent application Ser. No. 15/291,253 filed Oct. 12, 2016 which is incorporated by reference in its entirety herein.

FIELD OF THE INVENTION

The present subject matter relates generally to control and alteration of chemical properties of a resin.

BACKGROUND OF THE INVENTION

Additive manufacturing or 3D printing is often used for creating models using a liquid photopolymer resin (resin). The models may further be used as casting molds, prototypes, patterns, or end products. 3D printing is able to create complex designs of a desired surface finish that may not otherwise be created through other machining or manufacturing methods. For example, stereolithography (SLA) casting molds may be used to manufacture turbine airfoils.

When 3D printing is used to create casting molds, the quality of the resulting component produced by casting is at least in part dependent on the quality of the model. The quality of the model is at least in part dependent on the quality of the resin. While the quality, including chemical and physical characteristics, of the resin is generally known prior to production of models, as the resin ages, chemical and physical characteristics of the resin alter toward depletion, in which the resin loses its ability to produce models. Depletion of the resin results in an increased occurrence of model crashes, in which the resin of the model fails to properly cure or harden, resulting in a loss of geometry, tolerances, or desired surface finish, and ultimately discarding of the model and the resin. Depletion of the resin often occurs before the entire quantity of resin is consumed (i.e. the useful life of the resin is expiring before the physical quantity of resin is consumed), thereby resulting in wasted resin, scrapped models, and increased costs.

Therefore, a need exists for a system and method for controlling chemical properties of a resin as the resin ages.

BRIEF DESCRIPTION OF THE INVENTION

Aspects and advantages of the invention will be set forth in part in the following description, or may be obvious from the description, or may be learned through practice of the invention.

The present disclosure is directed to a method of altering chemical properties of an in-process resin used with a 3D printing apparatus. The method includes monitoring the in-process resin using an imaging spectrometer, comparing the in-process resin and a model using one or more spectrums from the imaging spectrometer, and diluting the in-process resin with a diluting resin.

A further aspect of the present disclosure is directed to a computer-implemented method of characterizing and altering chemical properties of an in-process resin used with a 3D printing apparatus. The computer-implemented method includes receiving, by one or more computing devices, one or more first spectrums from an imaging spectrometer, in which the one or more first spectrums define at least one absorbance value versus a wavenumber for the in-process resin. The computer-implemented method further includes receiving, by one or more computing devices, one or more second spectrums from the imaging spectrometer, in which the one or more second spectrums define at least one absorbance value versus a wavenumber for a model. The computer-implemented method further includes identifying, by one or more computing devices, a standard peak based at least in part on comparing the one or more first spectrums and the one or more second spectrums; identifying, by one or more computing devices, at least one chemical constituent peak indicating depletion of a chemical constituent based at least in part on comparing the one or more first spectrums and the one or more second spectrums; determining, by one or more computing devices, at least one peak ratio based at least in part on the standard peak and at least one chemical constituent peak; and generating, by one or more computing devices, a life cycle of the in-process resin based at least on an operating range of the at least one peak ratio.

A still further aspect of the present disclosure is directed to a system for characterizing and controlling chemical properties of an in-process resin. The system includes a 3D printing apparatus including the in-process resin and configured to generate a model, an imaging spectrometer configured to output at least one spectrum defining at least one absorbance value versus a wavenumber for each of the in-process resin and the model, and a computing device configured to operate the 3D printing apparatus and the imaging spectrometer.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

Repeat use of reference characters in the present specification and drawings is intended to represent the same or analogous features or elements of the present invention.

DETAILED DESCRIPTION OF THE INVENTION

Reference now will be made in detail to embodiments of the invention, one or more examples of which are illustrated in the drawings. Each example is provided by way of explanation of the invention, not limitation of the invention.

In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "first", "second", and "third" may be used interchangeably to distinguish one component from another and are not intended to signify location or importance of the individual components.

Characterization and control methods and systems for chemical properties of a resin while in use with a 3D printing apparatus is generally provided. The methods and systems of characterization improve upon resin characterization and control by determining a life cycle of the resin in use with a 3D printer and returning the resin to a known and repeatable chemical state. Restoration to known, repeatable, and quantifiable chemical properties mitigates model crashes and prevents resin waste due to depletion of the resin prior to consumption of the resin.

Although the disclosure below references specific chemical constituents and compositions of a photopolymer resin, the present disclosure is applicable generally to resins used for 3D printing, additive manufacturing, and other polymeric systems, including, but not limited to, stereolithography (SLA), optical fabrication, photo-solidification, solid free-form fabrication, solid imaging, rapid prototyping, resin printing, fused deposition modeling (FDM), digital light processing (DLP), multi jet printing (MLP), and type printing.

Figure 1:
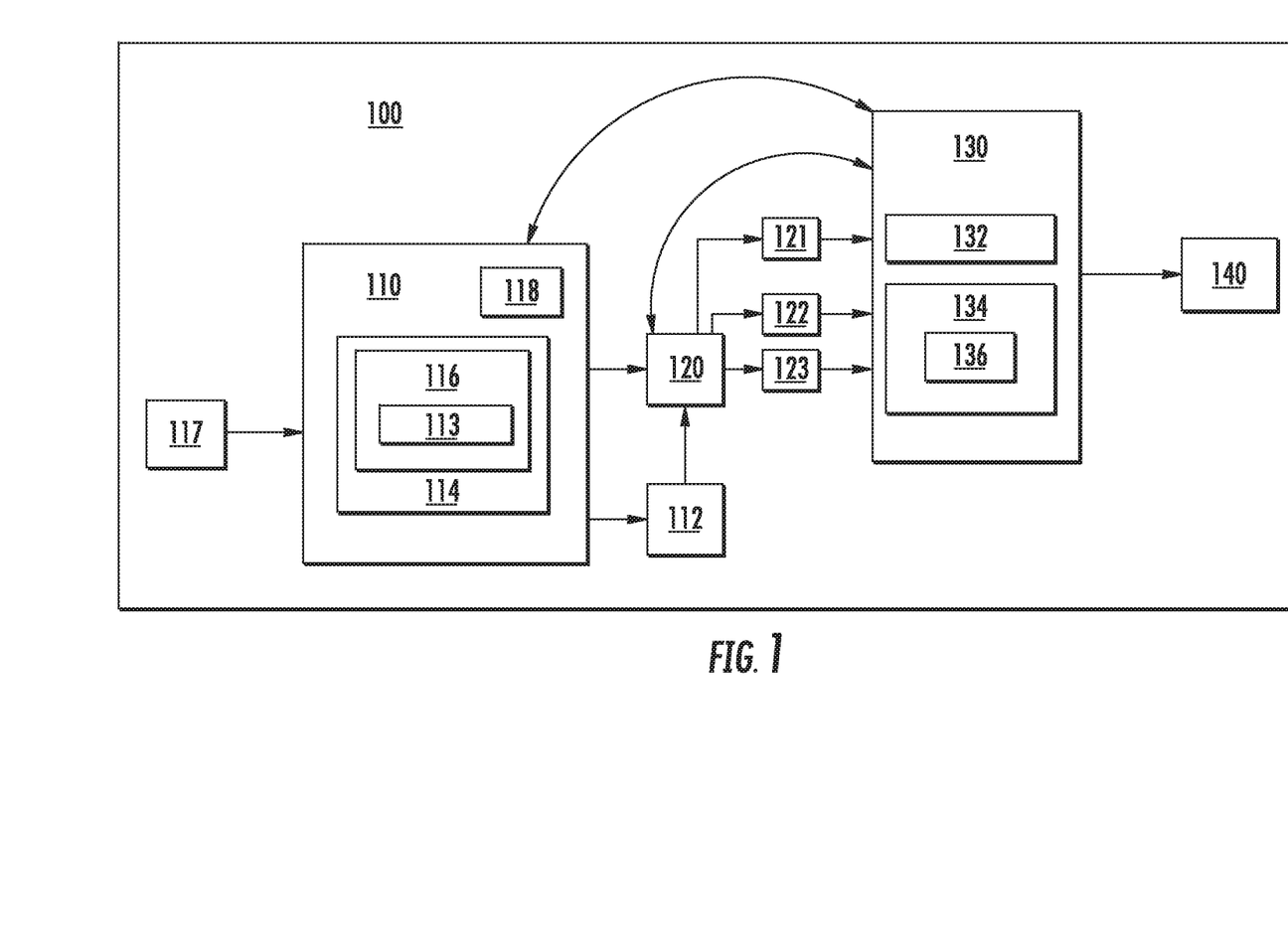
FIG. 1 is a diagram of an exemplary characterization and control system for a resin.

Referring now to the drawings, FIG. 1 is an exemplary embodiment of characterization and control system for a resin 100 (herein referred to as "system 100") used with a 3D printing apparatus 110 (herein referred to as "3D printer 110"). The system includes the 3D printer 110, an imaging spectrometer 120, and a computing device 130. The 3D printer 110 produces one or more models 112. The 3D printer 110 may include a platform 113 immersed in a vat 114 filled with an in-process resin 116, as a liquid photopolymer resin, and a nozzle 118. In one embodiment, the nozzle 118 exposes ultraviolet (UV) light to the in-process resin 116 in the vat 114 to produce the model 112 by curing the in-process resin 116. In various embodiments, the 3D printer 110 may further include an oven to bake the model 112 to further cure or harden the photopolymer resin within the model 112.

The system 100 further includes a computing device 130. The computing device 130 includes one or more processors 132 and one or more memory devices 134. The one or more memory devices 134 stores instructions 136 that, when executed by the one or more processors 132, cause the one or more processors to perform operations. The operations of the computing device 130 are further described herein.

In one embodiment of the system 100, the computing device 130 controls the 3D printer 110. In one example, a 3D model (e.g. CAD model) of a desired model 112 is uploaded to the computing device 130. The computing device 130 divides the 3D model into a multitude of thin layers. The computing device 130 controls, articulates, and operates the nozzle 118 to expose each thin layer of the in-process resin 116 to UV light, thereby curing the thin layer of the in-process resin 116 into a portion of the model 112. The computing device 130 may further control, articulate, and operate the platform 113 within the vat 114. The platform 113 may rotate or translate to further expose each thin layer of the in-process resin 116 to UV light in conjunction with operation of the nozzle 118.

In other embodiments of the 3D printer 110, the nozzle 118 deposits a quantity of the in-process resin 116 from the vat 114 onto the platform 113. The computing device 130 controls the nozzle 118 to deposit a quantity of the in-process resin 116 over a multitude of thin layers. The nozzle 118 may further include a light emitting or heat emitting source to cure the in-process resin 116.

In another embodiment of the system 100, the computing device 130 controls the imaging spectrometer 120. In various embodiments, the imaging spectrometer 120 is an infrared spectrometer. In still other embodiments, the imaging spectrometer 120 is a Fourier transform infrared spectrometer employing a Fourier transform infrared spectroscopy technique. In one embodiment, the infrared spectrometer encompasses a near-infrared range of about 14000 $cm^{-1}$ to about 4000 $cm^{-1}$. In another embodiment, the infrared spectrometer encompasses a mid-infrared range of about 4000 $cm^{-1}$ to about 400 $cm^{-1}$. In still another embodiment, the infrared spectrometer encompasses a far-infrared range of about 400 $cm^{-1}$ to about 10 $cm^{-1}$. In yet other embodiments, the infrared spectrometer may encompass a combination of overlapping ranges of the near-infrared, mid-infrared, or far-infrared ranges. In still yet other embodiments, the imaging spectrometer may define other ranges, conventions, or units to describe the portion of the electromagnetic spectrum in which the imaging spectrometer operates.

The imaging spectrometer 120 outputs one or more first spectrums 121 defining at least one absorbance or emissions value versus a spectral range of wavenumbers for the in-process resin 116. The first spectrum 121 may define a percentage ranging from about 0 to about 100, or its decimal equivalent, or any subset therebetween. The spectral range of wavenumbers may define a reciprocal centimeter.

The imaging spectrometer 120 outputs one or more second spectrums 122 defining at least one absorbance or emissions value versus a spectral range of wavenumbers for the model 112. In one embodiment, the second spectrum 122 for the model 112 is produced from a model 112 from an unused or new in-process resin 116. For example, the second spectrum 122 is produced from the model 112 in which the in-process resin 116 is of known chemical or physical characteristics prior to use to produce a plurality of models 112.

In various embodiment of the system 100, the computing device 130 determines one or more chemical constituents of the in-process resin 116 and correlates the one or more chemical constituents of the in-process resin 116 to at least one chemical constituent peak of the first spectrum and/or second spectrum. In one embodiment, the computing device 130 determines the one or more chemical constituents of the in-process resin 116 using a table, graph, chart, or document.

Figure 2:
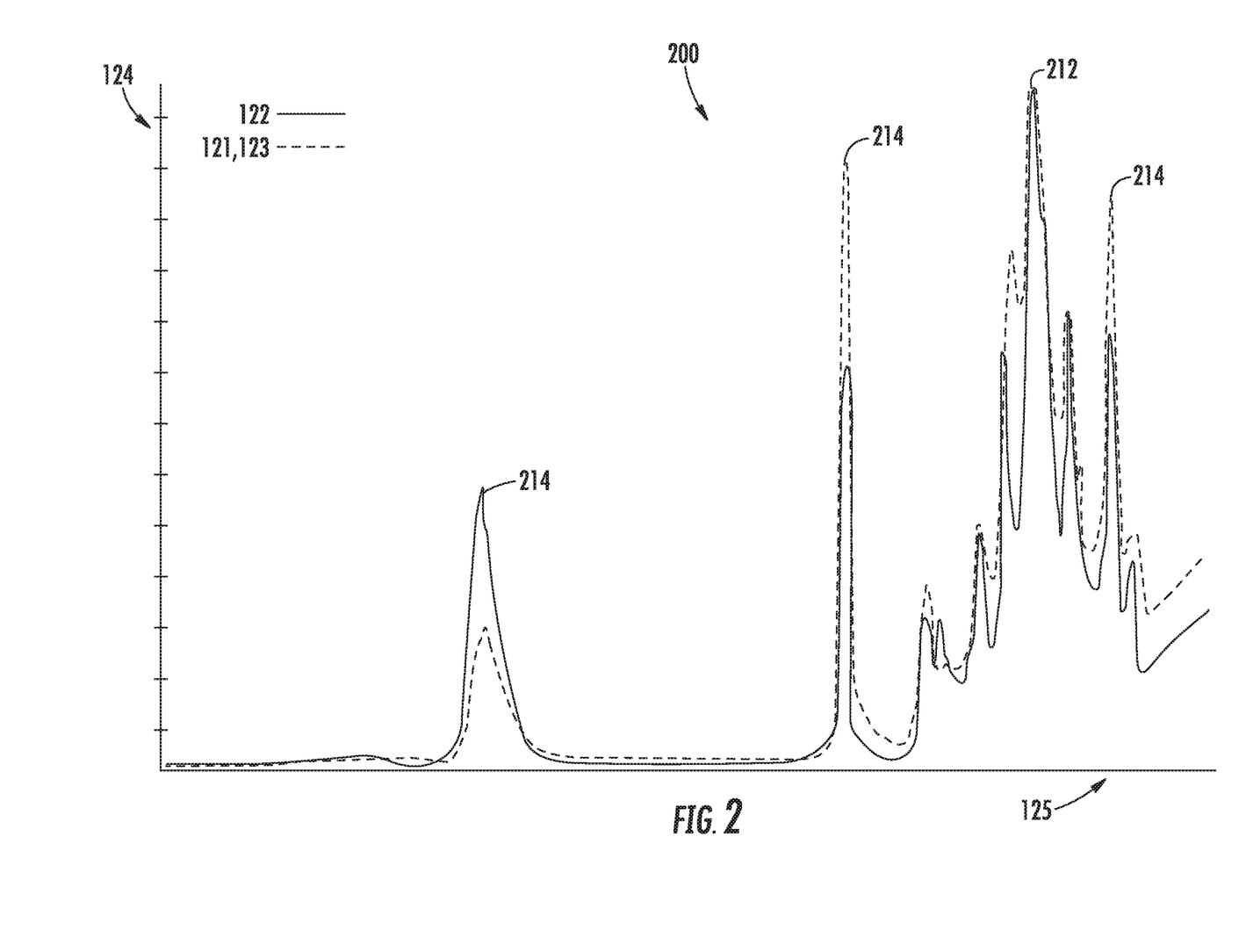
FIG. 2 is an exemplary spectrum from the exemplary system shown in FIG. 1.

Referring now to FIG. 2, an exemplary embodiment of a graph 200 of the first spectrum 121 and the second spectrum 122 is provided. In various embodiments, the first spectrum 121 and/or the second spectrum 122 may be provided in other formats, such as, but not limited to, comma separated value files, tables or tabulated data, spreadsheets, databases, or other graphical types, including at least an absorbance or emissions value corresponding to a wavenumber of a spectral range.

Referring to FIGS. 1 and 2, the computing device 130 of the system 100 identifies a standard peak based at least in part on comparing the one or more first spectrums and the one or more second spectrums. In one embodiment, the standard peak is identified by a plurality of chemical constituents contributing to the absorbance or emissions value of a peak of the first and/or second spectrum. In the exemplary embodiment shown in FIG. 2, the computing device 130 outputs the graph 200 as an overlay of the first spectrum 121 and the second spectrum 122. The standard peak 212 may appear where at least a substantial portion of chemical constituents contribute to an absorbance or emissions value 124 at a wavenumber value 125. In another embodiment in which the in-process resin 116 includes one or more chemical constituents defining an initiator chemical constituent and a reactive chemical constituent, the standard peak 212 may include a chemical bond that is common to the initiator chemical constituent and the reactive chemical constituent in the in-process resin 116. In yet another embodiment, the standard peak 212 may be defined as having a substantially similar absorbance value 124 for the first spectrum 121 compared to the second spectrum 122.

As a non-limiting example where the in-process resin 116 and the model 112 include 4,4'-Isopropylidenecyclohexanol, oligomeric reaction products with 1-chloro-2,3-epoxypropane; a 3-ethyl-3-hydroxymethyl oxetane; an ethoxylated trimethylolpropane triacrylate esters; a mixed triarylsulfonium hexafluorophosphate salts in propylene carbonate; and a 1-hydroxycyclohexyl phenyl ketone, a carbon-oxygen single bond stretch may appear in each chemical constituent and therefore contribute to the absorbance or emission value 124 of the standard peak 212 at a wavenumber 125 approximately similar between the first and second spectrums 121, 122.

Referring still to FIGS. 1 and 2, the computing device 130 of the system 100 identifies at least one chemical constituent peak 214 indicating depletion of a chemical constituent based at least in part on comparing the one or more first spectrums 121 and the one or more second spectrums 122. In various embodiments, the in-process resin 116 may include one or more of a solvent, an epoxy, and/or an oxetane.

In one embodiment, indications of depletion of a chemical constituent include indications of polymerization of the chemical constituents. In one embodiment including the aforementioned chemical constituents, an ammonia (CH) aromatic and a carbon-oxygen double bond in propylene carbonate may diminish from the first spectrum 121 to the second spectrum 122 at about the wavenumber for a chemical bond corresponding to a solvent in the initiator as a result of the polymerization process from the in-process resin 116 to the model 112. In another embodiment, indications of depletion of a chemical constituent including the aforementioned chemical constituents may diminish a reactive in the second spectrum 122 versus the first spectrum 121. In still another embodiment, indications of depletion of a chemical constituent may include a change in wavenumber in the second spectrum 122 versus the first spectrum 121 for a reactive chemical constituent. For example, referring still to the aforementioned chemical constituents, the second spectrum 122 may include a diminished magnitude of absorbance of a reactive chemical constituent due to a depletion of a carbon-oxygen single bond in an epoxy and/or oxetane.

Referring back to FIG. 1, the computing device 130 determines at least one peak ratio based at least in part on the standard peak and at least one chemical constituent peak. In one embodiment, the peak ratio is the absorbance of a chemical constituent peak divided by the absorbance at the standard peak. In another embodiment, the peak ratio is the absorbance of a reactive chemical constituent peak divided by the absorbance at the standard peak. In yet another embodiment, the peak ratio is the absorbance of an initiator chemical constituent peak divided by the absorbance at the standard peak.

The system 100 generates a life cycle 140 of the in-process resin 116 based on at least an operating range of the at least one peak ratio. In various embodiments, the computing device 130 generates the life cycle 140 of the in-process resin 116 based on one or more control charts (such as a control chart 141 shown in FIG. 4). In one embodiment, the life cycle 140 includes at least one peak ratio from a reactive chemical constituent peak. In another embodiment, the life cycle 140 includes at least one peak ratio from an initiator chemical constituent peak. In various embodiments, the life cycle 140 may include an upper control limit, a lower control limit, and/or a moving range. In other embodiments, the life cycle 140 may include an average moving range.

Figure 3:
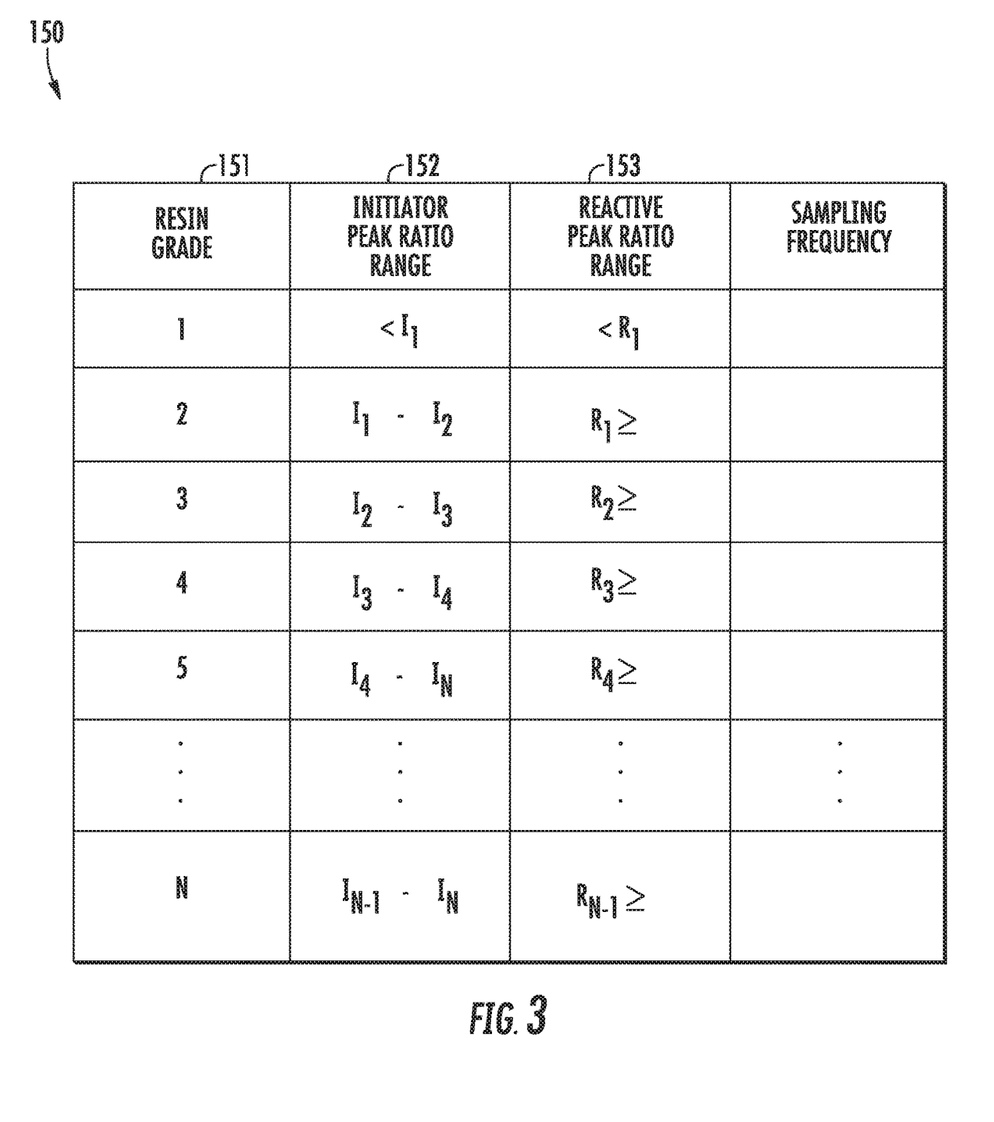
FIG. 3 is an exemplary resin gradation generated from the exemplary system shown in FIG. 1.

In various embodiments of the system 100, the computing device 130 generates the life cycle 140 of the in-process resin 120 including a resin gradation (such as a resin gradation 150 shown in FIG. 3) based at least on an operating range of the at least one peak ratio and one or more standard deviations of the at least one peak ratio. Referring now to FIGS. 1 and 3, in one embodiment, resin gradation 150 may be defined by ranges of peak ratios 152, 153 determined by the computing device 130. The resin gradation 150 may define a plurality of resin grades 151. In the embodiment shown in FIG. 3, the resin gradation 150 defines at (152) a Grade 1 resin by a first initiator peak ratio range less than $I_1$; a Grade 2 resin may be defined by a second initiator peak ratio range between $I_1$ and $I_2$; a Grade 3 resin may be defined by a third initiator peak ratio range between $I_2$ and $I_3$; and etc. until a Grade N resin may be defined by an Nth initiator peak ratio range between $I_{N-1}$ and $I_N$. In another embodiment, the resin gradation 150 defines at (153) a Grade 1 resin may be defined by a first reactive peak ratio range less than $R_1$; a Grade 2 resin may be defined by a second reactive peak ratio range greater than $R_1$; a Grade 3 resin may be defined by a third reactive peak ratio range greater than $R_2$; and etc. until a Grade N resin may be defined by reactive peak ratio range greater than $R_{N-1}$.

Figure 4:
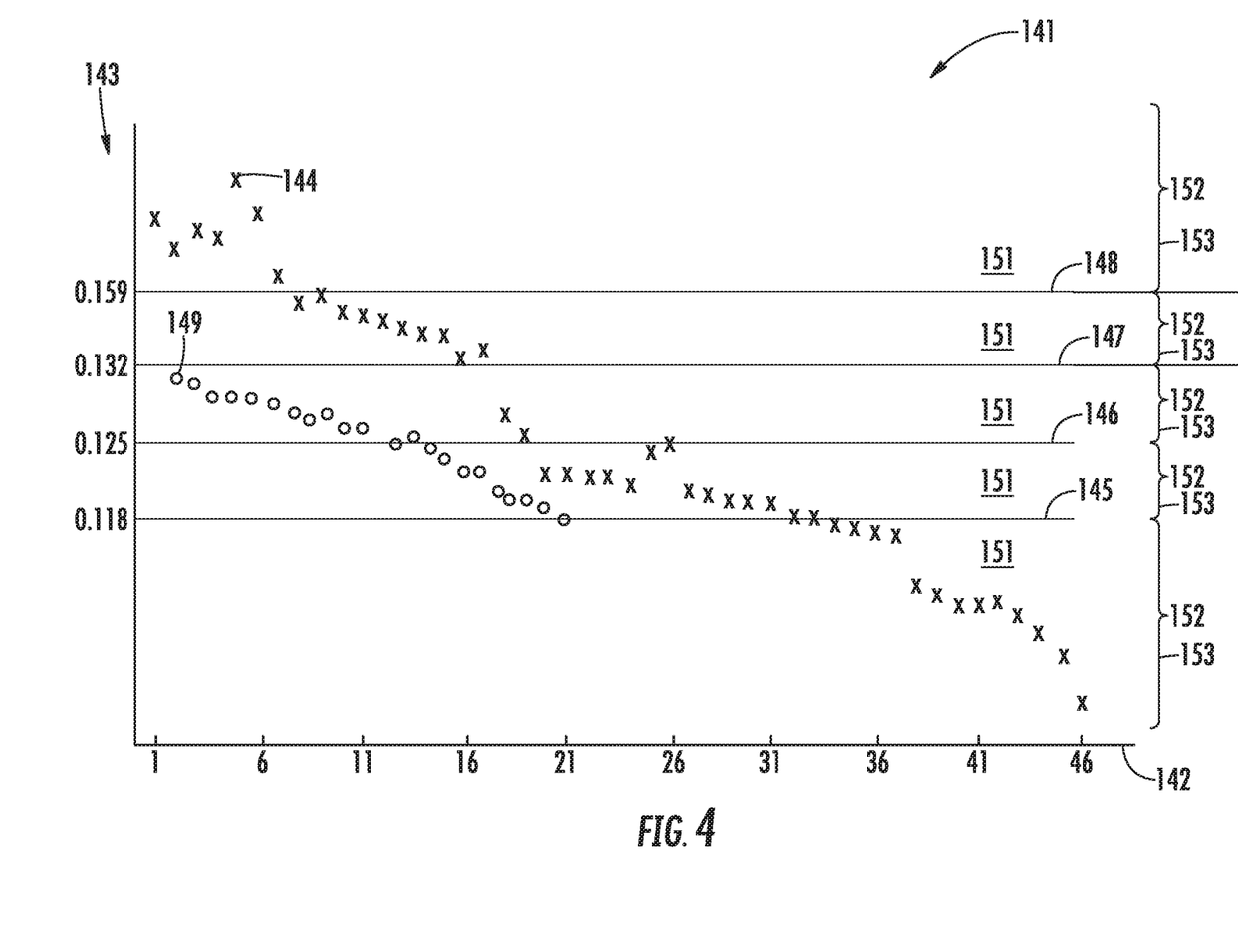
FIG. 4 is an exemplary control chart generated from the exemplary system shown in FIG. 1.

Referring now to FIGS. 1 and 4, the system 100 determines whether the in-process resin 116 is unexpired or expiring based at least on the life cycle 140 of the in-process resin 116. In one embodiment, the computing device 130 determines whether the in-process resin 116 is unexpired or expiring based at least on one or more control charts 141. The control chart 141 may include a time-dependent axis 142 and an axis of peak ratios 143. The control chart 141 may include one or more peak ratios 144. In various embodiments, the computing device 130 defines a peak ratio limit 145 at about or below which the in-process resin 116 is expiring. In one embodiment, the in-process resin 116 is expired when one or more peak ratios 144 is at about or below a peak ratio limit 145 defined by a lower control limit of the peak ratios. In another embodiment, the in-process resin 116 is expired when one or more peak ratios 144 is at about or below a peak ratio limit 145 defined by three standard deviations below a median. In still other embodiments, the in-process resin 116 is expired when one or more peak ratios 144 corresponding to a reactive chemical constituent and/or an initiator chemical constituent is at about or below the peak ratio limit 145. In various embodiments, the peak ratios 144 are determined from a reactive chemical constituent or an initiator chemical constituent from the in-process resin 116.

Referring to FIGS. 3 and 4, in various embodiments, the resin gradation 150 or the control chart 141 may further define resin grades 151 or ranges of peak ratios 152, 153 by a number of standard deviations from the median of a sample population of peak ratios of the first quantity of resin 120. As a non-limiting example, where the median peak ratio for the initiator chemical constituent is approximately 0.125 and approximately 99.7 percent (or three standard deviations) of a normal distribution of the sample population is desired to be captured of the peak ratios, a peak ratio at or below three standard deviations below the median may define a Grade 1 resin; a range from the median to three standard deviations below the median may define a Grade 2 resin; a range from the median to three standard deviations above the median may define a Grade 3 resin; a range of an additional three standard deviations above Grade 3 may define a Grade 4 resin; and a range of an additional three standard deviations above Grade 4 may define a Grade 5 resin. As another non-limiting example, a Grade 5 resin may be defined by a range of peak ratios 152, 153 for a sample population of the unused in-process resin 116 (i.e. not previously used to create the model 112), or the in-process resin 116 used approximately once (i.e. used once previously to create the model 112).

Referring to FIG. 1, the system 100 dilutes the in-process resin 116 with a diluting resin 117 based at least on whether the in-process resin 116 is unexpired or expiring. In various embodiments, diluting the in-process resin 116 with the diluting resin 117 includes employing a rule of mixtures. In one embodiment, the diluting resin 117 is an unused liquid photopolymer resin. In another embodiment, the diluting resin 117 is a previously used liquid photopolymer resin. In various embodiments, the diluting resin 117 includes similar chemical constituents as the in-process resin 116.

In various embodiments of the system 100, the computing device 130 receives one or more of a third spectrum 123 from the imaging spectrometer 120, in which the one or more third spectrum 123 defines at least one absorbance value versus a wavenumber for the diluting resin 117. The computing device 130 further determines at least one peak ratio for the diluting resin 117 based at least in part on the standard peak 212 and at least one chemical constituent peak identified with the in-process resin 116. The computing device 130 may further determine a range of peak ratios for the diluting resin 117 from which to dilute the in-process resin 116.

In one embodiment of the system 100, the computing device 130 determines the range of peak ratios for the diluting resin 117 from which to dilute the in-process resin 116 using a rule of mixtures. In another embodiment, using a rule of mixtures may include using the at least one peak ratio of the diluting resin 117 and using the at least one peak ratio of the in-process resin 116.

As a non-limiting example, a rule of mixtures is employed to calculate a quantity (e.g. weight, volume, etc.) of the diluting resin 117 at a known peak ratio with which to dilute with a known quantity of the in-process resin 116. In one embodiment, a rule of mixtures is employed to determine a quantity of diluting resin 117 to achieve a desired peak ratio for the in-process resin 116. In another embodiment, a rule of mixtures is employed to determine a quantity of diluting resin 117 to achieve a desired resin grade 151 for the in-process resin 116 from the resin gradation 150.

Referring now to FIGS. 1-4, the diluting resin 117 and the one or more third spectrum 123 may be implemented, configured, or otherwise executed substantially similarly as described in referenced to the in-process resin 116 and/or the one or more first spectrum 121. Additionally, as shown in FIG. 4, the control chart 141 may further include post-dilution peak ratios 149 demonstrating the return of the chemical characterization of the in-process resin 116 to a known state following dilution with the diluting resin 117.

Figure 5:
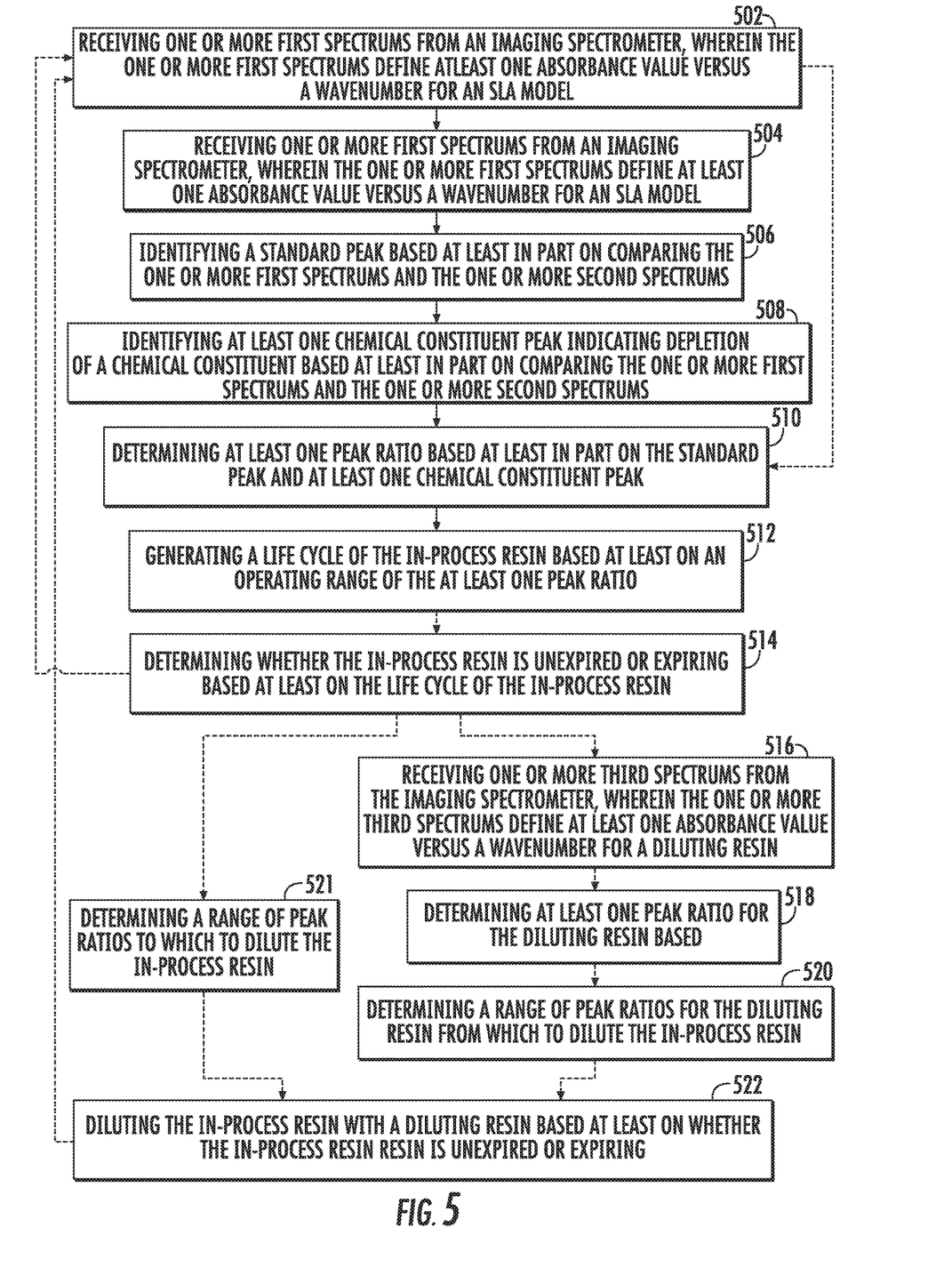
FIG. 5 is a flowchart outlining steps performed by the disclosed method of characterization and control of chemical properties of a resin.

Referring now to FIG. 5, a flowchart outlining exemplary steps of a method to characterize and control chemical properties of an in-process resin 500 (herein referred to as "method 500") is provided. The flowchart of FIG. 5 may be implemented by one or more computing devices, such as the computing device 130 depicted and described relative to FIGS. 1 and 6. FIG. 5 depicts steps performed in a particular order for the purposes of illustration and discussion. Those of ordinary skill in the art, using the disclosures provided herein, will understand that various steps of any of the methods disclosed herein can be adapted, modified, rearranged, omitted, or expanded in various ways without deviating from the scope of the present disclosure.

The method 500 can include monitoring an in-process resin using an imaging spectrometer, comparing the in-process resin and a model using one or more spectrums from the imaging spectrometer, and diluting the in-process resin with a diluting resin. The method 500 can include at (502) receiving one or more first spectrums from an imaging spectrometer. The one or more first spectrums define at least one absorbance value versus a wavenumber for an in-process resin. At (504), the method 500 can include receiving one or more second spectrums from the imaging spectrometer. The one or more second spectrums define at least one absorbance value versus a wavenumber for a model. For example, the one or more second spectrums 122 produced by the system 100 described in regard to FIGS. 1 and 2 may be produced from an imaging spectroscopy of the model 112 from the imaging spectrometer 120. The model 112 may represent a baseline or desired output from the 3D printer 110 of which may be desirably repeated with the in-process resin 116.

The method 500 can include at (506) identifying a standard peak based at least in part on comparing the one or more first spectrums and the one or more second spectrums. At (508), the method 500 can include identifying at least one chemical constituent peak indicating depletion of a chemical constituent based at least in part on comparing the one or more first spectrums and the one or more second spectrums. In various embodiments, the method 500 may further include comparing the one or more first spectrums and the one or more second spectrums at corresponding wavenumbers. In one embodiment, comparing the one or more first spectrums and the one or more second spectrums may include comparing at ranges of wavenumbers to identify changes in magnitude of absorbance or emissions and/or identifying changes, or shifts, in wavenumbers relative to a magnitude of absorbance or emission.

The method 500 can include at (510) determining at least one peak ratio based at least in part on the standard peak and at least one chemical constituent peak. For instance, determining at least one peak ratio may include determining a peak ratio based on the standard peak and a reactive chemical constituent peak. In another instance, determining at least one peak ratio may include determining a peak ratio based on the standard peak and an initiator chemical constituent peak. In still another instance, determining a peak ratio may include repeating one or more steps of the method 500 over a period of time.

At (512), the method 500 can include generating a life cycle of the in-process resin based at least on an operating range of the at least one peak ratio. In one embodiment, generating the life cycle of the in-process resin includes generating a resin gradation based at least on an operating range of the at least one peak ratio and one or more standard deviations of the at least one peak ratio.

In various embodiments, the method 500 may further include at (514) determining whether the in-process resin is unexpired or expiring based at least on the life cycle of the in-process resin. For instance, determining whether the in-process resin is unexpired or expiring may include comparing a peak ratio to an operating range of the life cycle. In another instance, determining whether the in-process resin is unexpired or expiring may include comparing a peak ratio to a resin gradation. In still another instance, determining whether the in-process resin is unexpired or expiring may include comparing a peak ratio to a lower limit.

In another embodiment, the method 500 may further include at (516) receiving one or more third spectrums from the imaging spectrometer. The one or more third spectrums define at least one absorbance value versus a wavenumber for a diluting resin. At (518), the method 500 may include determining at least one peak ratio for the diluting resin based at least in part on the standard peak and at least one chemical constituent peak identified with the in-process resin.

At (520), the method 500 may include determining a range of peak ratios for the diluting resin from which to dilute the in-process resin. In one embodiment in which the vat 114 is limited by volume and/or weight, determining a range of peak ratios for the diluting resin from which to dilute the in-process resin includes determining a minimum peak ratio of the diluting resin sufficient to dilute the in-process resin to a desired peak ratio and within the constraints of the vat 114 or system 100. In another embodiment, determining a range of peak ratios for the diluting resin from which to dilute the in-process resin may include determining a quantity of diluting resin of a known peak ratio necessary to dilute the in-process resin to a desired range of peak ratio.

The method 500 may include at (521) determining a range of peak ratios to which to dilute the in-process resin. In one embodiment, a user may input to the computing device 130 a desired range of peak ratios to which to dilute the in-process resin 116. In another embodiment, the computing device 130 may determine a range of peak ratios to which to dilute the in-process resin 116 based at least on the life cycle 140. For instance, the range of peak ratios to which to dilute the in-process resin 116 may be a defined range from an operating range of the in-process resin 116. As another non-limiting example, the range of peak ratios 152, 153 may be determined or chosen from the life cycle 140, such as, but not limited to, from the control chart or the resin gradation.

The method 500 may include at (522) diluting the in-process resin with a diluting resin based at least on whether the in-process resin is unexpired or expiring. For instance, the computing device 130 of the system 100 may transmit a signal to the 3D printer 110 to mix the diluting resin 117 and the in-process resin 116 by determined quantities and/or to determined ranges of peak ratios.

At (524), the method 500 may further include determining one or more chemical constituents of the in-process resin. At (526), the method 500 may include correlating the one or more chemical constituents of the in-process resin to at least one chemical constituent peak of the first spectrum and/or second spectrum.

In various embodiments, the method 500 or portions thereof may be performed iteratively. In one embodiment, the steps at (502), (504), (506), (508), (510), and (512) may be performed iteratively. In another embodiment, the aforementioned steps and (514) may be performed iteratively. In still another embodiment, the aforementioned steps may be performed and a portion of the steps, such as at (502), (510), (512), and (514) may be performed iteratively thereafter.

Figure 6:
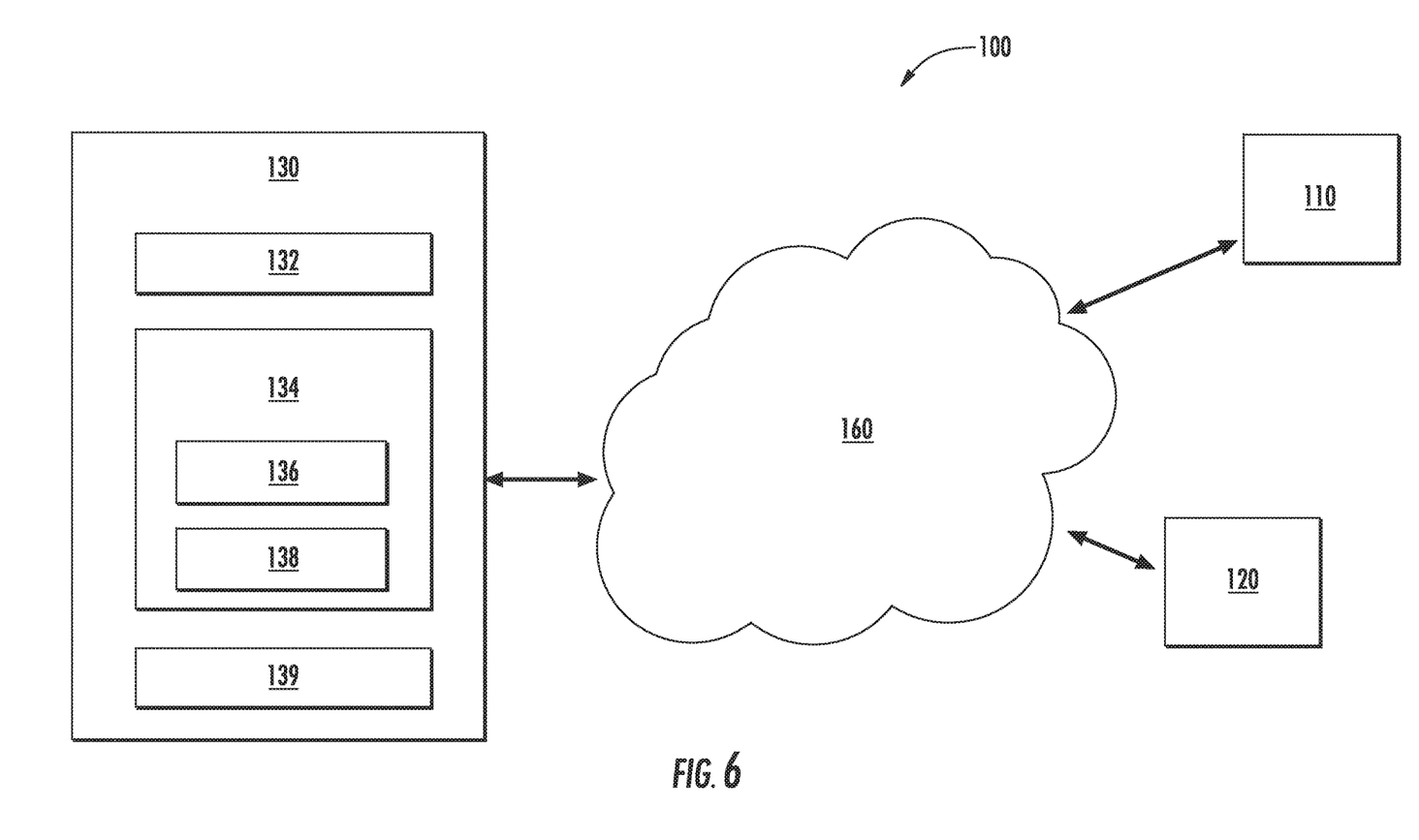
FIG. 6 is another exemplary embodiment of a characterization and control system for a resin.

Referring now to FIG. 6, another exemplary embodiment of a characterization and control system 100 for a photopolymer resin is provided. The system 100 may include a 3D printer 110, an imaging spectrometer 120, and a computing device 130. The system 100 may further include one or more networks 160 to communicate within the system 100 and/or externally of the system 100. The one or more processors 132 can include any suitable processing device, such as a microprocessor, microcontroller, integrated circuit, logic device, and/or other suitable processing device. The one or more memory devices 134 can include one or more computer-readable media, including, but not limited to, non-transitory computer-readable media, RAM, ROM, hard drives, flash drives, non-volatile storage devices, and/or other memory devices.

The system 100 may communicate via one or more network(s) 160, which can include any suitable wired and/or wireless communication links for transmission of the communications and/or data, as described herein. For instance, the network 160 may include a SATCOM network, ACARS network, ARINC network, SITA network, AVICOM network, a VHF network, a HF network, a Wi-Fi network, a WiMAX network, a gatelink network, etc.

The one or more memory devices 134 can store information accessible by the one or more processors 132, including computer-readable instructions 136 that can be executed by the one or more processors 132. The instructions 136 can be any set of instructions that when executed by the one or more processors 132, cause the one or more processors 132 to perform operations. In some embodiments, the instructions 136 can be executed by the one or more processors 132 to cause the one or more processors 132 to perform operations, such as any of the operations and functions for which the system 100 and/or the computing device 130 are configured, the operations for characterizing and controlling chemical properties of a photopolymer resin (e.g., method 400), as described herein, the system for generating the life cycle of a photopolymer resin and/or diluting a photopolymer resin (e.g., system 100), the characterization and control system for a photopolymer resin, and/or any other operations or functions of the one or more computing device 130. The instructions 136 can be software written in any suitable programming language or can be implemented in hardware. Additionally, and/or alternatively, the instructions 136 can be executed in logically and/or virtually separate threads on one or more processors 132. The one or more memory devices 134 can further store data 138 that can be accessed by the processor(s) 132. For example, the data 138 can include the first spectrum 121, the second spectrum 122, the third spectrum 123, the standard peak 212, the chemical constituent peaks 214, the absorbance or emissions values 124, the wavenumber values 125, the one or more ranges of peak ratios 152, 153, the life cycle 140, the control charts 141, the resin gradation 150, and/or any other data and/or information described herein.

The computing device 130 can also include a network interface 139 used to communicate, for example, with the other components of system 100 (e.g., via network 160). The network interface 139 can include any suitable components for interfacing with one or more networks, including for example, transmitters, receivers, ports, controllers, antennas, and/or other suitable components.

The technology discussed herein makes reference to computer-based systems and actions taken by and information sent to and from computer-based systems. One of ordinary skill in the art will recognize that the inherent flexibility of computer-based systems allows for a great variety of possible configurations, combinations, and divisions of tasks and functionality between and among components. For instance, processes discussed herein can be implemented using a single computing device or multiple computing devices working in combination. Databases, memory, instructions, and applications can be implemented on a single system or distributed across multiple systems. Distributed components can operate sequentially or in parallel.

The systems 100 and methods 500 shown in regard to FIGS. 1-6 and described herein may characterize and control chemical properties of an in-process resin as the chemical properties alter over time. The systems and methods described herein may return the in-process resin to known and desirable chemical properties following alteration to an unknown state. Additionally, the method of diluting the in-process resin with the diluting resin provides benefits over alternative methods. For example, since 3D printing, including vats, is generally limited by physical properties such as space, weight, or volume, the methods and systems disclosed may improve resin characteristics within a limited physical space. Additionally, the methods and systems disclosed may return the in-process resin to a known chemical state and known state of the in-process life cycle in contrast to other methods. Still further, the methods and systems disclosed may reduce waste, and thereby provide cost benefits, over other methods of dilution or characterization.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method of altering chemical properties of an in-process resin used with a 3D printing apparatus, the method comprising:
    monitoring the in-process resin using an imaging spectrometer;
    determining at least one peak ratio based at least in part on a standard peak and at least one chemical constituent peak;
    generating a life cycle of the in-process resin based at least on an operating range of the at least one peak ratio, an upper control limit, and a lower control limit;
    comparing the in-process resin and a model using one or more spectrums from the imaging spectrometer;
    determining, based on the comparison of the in-process resin and the model, whether the in-process resin is unexpired or expiring based at least on the life cycle of the in-process resin;
    diluting the in-process resin with a diluting resin;
    receiving one or more third spectrums from the imaging spectrometer, wherein the one or more third spectrums define at least one absorbance value versus a wavenumber for the diluting resin;
    determining the at least one peak ratio for the diluting resin based at least in part on the standard peak and the at least one chemical constituent peak identified with the in-process resin; and
    determining a range of peak ratios for the diluting resin from which to dilute the in- process resin.

2. The method of claim 1, further comprising:
    identifying the standard peak based at least in part on comparing one or more first spectrums and one or more second spectrums from the imaging spectrometer.

3. The method of claim 1, further comprising:
    identifying the at least one chemical constituent peak indicating depletion of a chemical constituent based at least in part on comparing one or more first spectrums and one or more second spectrums from the imaging spectrometer.

4. The method of claim 1, further comprising:
    determining a range of peak ratios to which to dilute the in-process resin with the diluting resin.

5. The method of claim 1, wherein determining the range of peak ratios for the diluting resin from which to dilute the in-process resin comprises determining a quantity of the diluting resin of a known peak ratio to dilute the in-process resin to a range of peak ratios.

6. The method of claim 1, wherein determining the range of peak ratios for the diluting resin from which to dilute the in-process resin includes using a rule of mixtures.

7. The method of claim 1, wherein the life cycle further includes a moving range.

8. The method of claim 1, wherein the life cycle further includes an average moving range.

9. The method of claim 1, wherein the life cycle includes a resin gradation based at least on an operating range of the at least one peak ratio and one or more standard deviations of the at least one peak ratio.

10. The method of claim 1, wherein the diluting resin includes chemical constituents included in the in-process resin.

11. A method of altering chemical properties of an in-process resin used with a 3D printing apparatus, the method comprising:
    monitoring the in-process resin using an imaging spectrometer;
    determining at least one peak ratio based at least in part on a standard peak and at least one chemical constituent peak;
    generating a life cycle of the in-process resin based at least on an operating range of the at least one peak ratio;
    comparing the in-process resin and a model using one or more spectrums from the imaging spectrometer;
    diluting the in-process resin with a diluting resin;
    receiving one or more third spectrums from the imaging spectrometer, wherein the one or more third spectrums define at least one absorbance value versus a wavenumber for the diluting resin; and
    determining the at least one peak ratio for the diluting resin based at least in part on the standard peak and the at least one chemical constituent peak identified with the in-process resin; and
    determining a range of peak ratios for the diluting resin from which to dilute the in- process resin.

12. The method of claim 11, further comprising:
    identifying the standard peak based at least in part on comparing one or more first spectrums and one or more second spectrums from the imaging spectrometer.

13. The method of claim 11, further comprising:
identifying the at least one chemical constituent peak indicating depletion of a chemical constituent based at least in part on comparing one or more first spectrums and one or more second spectrums from the imaging spectrometer.

14. The method of claim 11, wherein determining the range of peak ratios for the diluting resin from which to dilute the in-process resin includes using a rule of mixtures.

15. The method of claim 11, wherein the life cycle further includes a moving range.

16. The method of claim 11, wherein the life cycle further includes an average moving range.

17. The method of claim 11, wherein the life cycle includes a resin gradation based at least on an operating range of the at least one peak ratio and one or more standard deviations of the at least one peak ratio.

18. The method of claim 11, wherein the diluting resin includes chemical constituents included in the in-process resin.

\* \* \* \* \*